United States Patent
Krauter et al.

[11] Patent Number: 5,840,012
[45] Date of Patent: Nov. 24, 1998

[54] DIAGNOSTIC INSTRUMENT SUPPORTING SYSTEM

[75] Inventors: Allan I. Krauter, Syracuse; Michael Kehoskie, Jordan; Jon R. Salvati, Skaneateles Falls; Scott Ryan, Skaneateles; Deborah A. Laun, Syracuse; Frank J. Witkowski, III, Marcellus, all of N.Y.

[73] Assignee: Welch Allyn, Inc., Skaneateles Falls, N.Y.

[21] Appl. No.: 748,375

[22] Filed: Nov. 13, 1996

[51] Int. Cl.⁶ ................................................. A61B 1/00
[52] U.S. Cl. .................................................. 600/102
[58] Field of Search .................................. 600/101, 102, 600/109, 114, 103, 117, 105, 227; 354/293, 294; 433/77, 79

[56] References Cited

U.S. PATENT DOCUMENTS

| | | | |
|---|---|---|---|
| 3,994,288 | 11/1976 | Stumpf | 128/6 |
| 4,491,131 | 1/1985 | Vassiliadis | 606/10 |
| 4,854,301 | 8/1989 | Nakajima | 600/102 |
| 4,907,395 | 3/1990 | Opie et al. | 600/102 X |
| 5,143,054 | 9/1992 | Adair | 128/18 |
| 5,441,042 | 8/1995 | Putman | 600/102 |
| 5,540,649 | 7/1996 | Bonnell et al. | 600/102 X |
| 5,571,072 | 11/1996 | Kronner | 600/102 |

FOREIGN PATENT DOCUMENTS

| | | | |
|---|---|---|---|
| 724652 | 9/1942 | Germany | 600/102 |
| 6-63003 | 3/1994 | Japan | 600/102 |

*Primary Examiner*—Beverly M. Flanagan
*Attorney, Agent, or Firm*—Wall Marjama & Bilinski

[57] ABSTRACT

A diagnostic instrument system includes a compact instrument housing having an interior for containing an illumination system and an optical viewing system for illuminating and viewing a target, both systems being arranged within the housing. The housing is separably and interchangeably mounted to a pair of supporting stand fixtures, each fixture having interfacing handle portions to which the instrument can be selectively attached without modification. The interfacing handle portions include electrical and video connections which interface with the optical and illumination systems of the instrument housing when attached to either fixture.

10 Claims, 7 Drawing Sheets

DIAGNOSTIC INSTRUMENT SUPPORTING SYSTEM

FIELD OF THE INVENTION

The invention relates to diagnostic instruments, and in particular to a diagnostic instrument system allowing interchangeable use with separate supporting apparatus.

BACKGROUND OF THE INVENTION

Known diagnostic instruments are designed for examining regions which are not easily inspectable. Applications include the automotive, medical, scientific, and military fields, among others. A colposcope is an example of a medical diagnostic instrument which is used to examine the vaginal area of a patient. The scope contains viewing optics to allow visual inspection of the cervix and an illumination system for projecting light onto the targeted area.

Commonly known colposcopes, however, particularly those having video capability, are provided as an integral part of a large dedicated apparatus, having limited mobility and versatility. In addition, such systems require a significant footprint which seriously impacts the availability of space, particularly within the confines of a doctor's office or other similar environment.

There is a need, therefore, to provide a diagnostic instrument system, such as a colposcope, which is compact and adaptable for use in a variety of settings, and which is mobile to allow easy storage, such as for use in a doctor's office in which space is a premium.

SUMMARY OF THE INVENTION

A primary object of the present invention is to provide a system for a clinical diagnostic instrument, such as a compact video colposcope, which is adapted to allow supporting attachment onto at least two different supporting platforms.

Another primary object of the present invention is to provide a compact colposcope body having a common electrical connection for a number of power inputs, as well as for video and other signal outputs from the colposcope body.

Another primary object of the present invention is to provide a fastening support for a colposcope or other diagnostic instrument which allows simple and unique assembly and disassembly.

Still another primary object of the present invention is to provide a mechanical interlock for a diagnostic instrument which prevents lamp replacement without first separating the body of the instrument from the support fixturing.

Yet another primary object of the present invention is to provide a means for separating the instrument body from the support fixturing, to allow access to the lamp for replacement. Preferably, the separation also disables the illumination system until the instrument has been restored to the support fixturing, in order to promote safety.

Therefore, and according to a preferred aspect of the present invention, there is provided a diagnostic instrument system comprising:
  a diagnostic instrument having a housing including an interior, an illumination system arranged within said interior for illuminating a target, and an optical system adjacently arranged within said interior relative to said illumination system for viewing the illuminated target;
  at least two supporting fixtures, said supporting fixtures each having an interfacing handle portion engageable with different surfaces of said housing for attachment thereto; and
  means for releasably attaching said housing to either of said supporting fixtures.

According to another preferred aspect of the present invention, there is provided a colposcopic system comprising a compact colposcope having an interior for containing an illumination system and an adjacently arranged optical system, and a pair of supporting assemblies wherein said body includes means for allowing the colposcope to be selectively attached to either of said supporting assemblies.

Preferably, each supporting assembly includes an interfacing handle portion which engages the colposcope body to provide a mechanical support, as well as provide electrical and video interconnection between the compact body and an electrical power supply and a set of peripheral devices. One of the fixtures is a swing arm supporting fixture which supports the top and rear sides of the colposcope body, and the remaining supporting assembly supports the bottom and rear sides of the body.

According to another preferred aspect of the present invention, there is provided a colposcope assembly comprising:
  a colposcope including a housing having an interior, an illumination system for illuminating a target and an optical system for viewing said target, said illumination and optical systems being disposed adjacently within said housing;
  a first supporting fixture for supporting said colposcope housing;
  a second supporting fixture for supporting said colposcope housing; and
  adapter means for selectively attaching said colposcope housing to either of said supporting fixtures.

In a preferred feature of the present invention, the colposcope includes an illumination system including a lamp contained within the housing including a removable lamp access door. When the lamp access door is removed, a pair of microswitches are opened, preventing the lamp from being powered until the door is reattached.

An advantageous aspect of the present invention is that the colposcope or other diagnostic instrument is easily attachable and detachable from at least a pair of separate supporting fixtures, which allow support of the scope in a variety of orientations.

Another advantage of the present invention is that the colposcope and supporting assemblies are movable and portable, allowing for easy storage and maximizing the use of an office environment.

These and other objects, features, and advantages are herein described in the following Detailed Description of the Invention along with the accompanying drawings.

DETAILED DESCRIPTION OF THE INVENTION

The following description refers to a preferred embodiment of a diagnostic instrument system, specifically describing a colposcope, though it will be readily apparent that the concepts described are applicable to other apparatus. During the course of discussion herein, several terms such as "upper", "lower", "top", "bottom", "front", "behind", "above", and "below" are used to provide a frame of reference for the accompanying FIGS. These terms are not intended to be limiting and are provided to clarify the discussion of the operation of the present invention.

Figure 1:
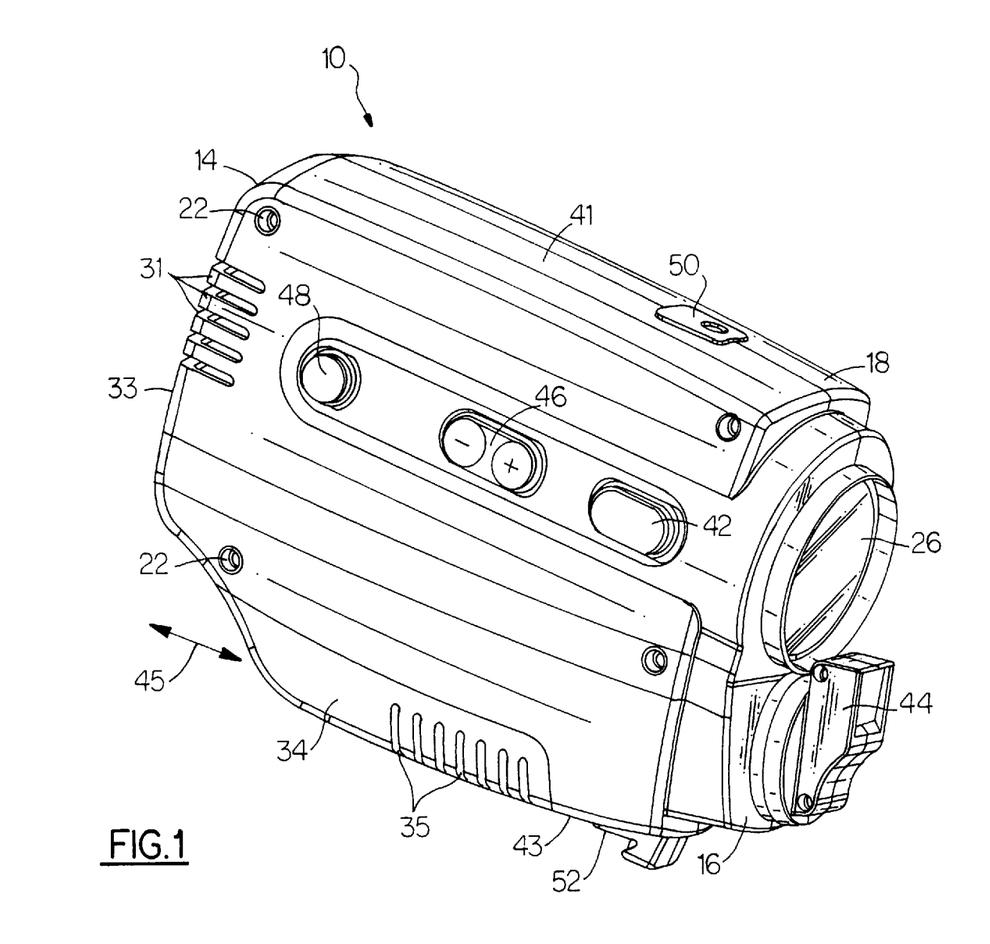
FIG. 1 is a top perspective view of a compact video colposcope in accordance with a preferred aspect of the present invention.
Figure 2:
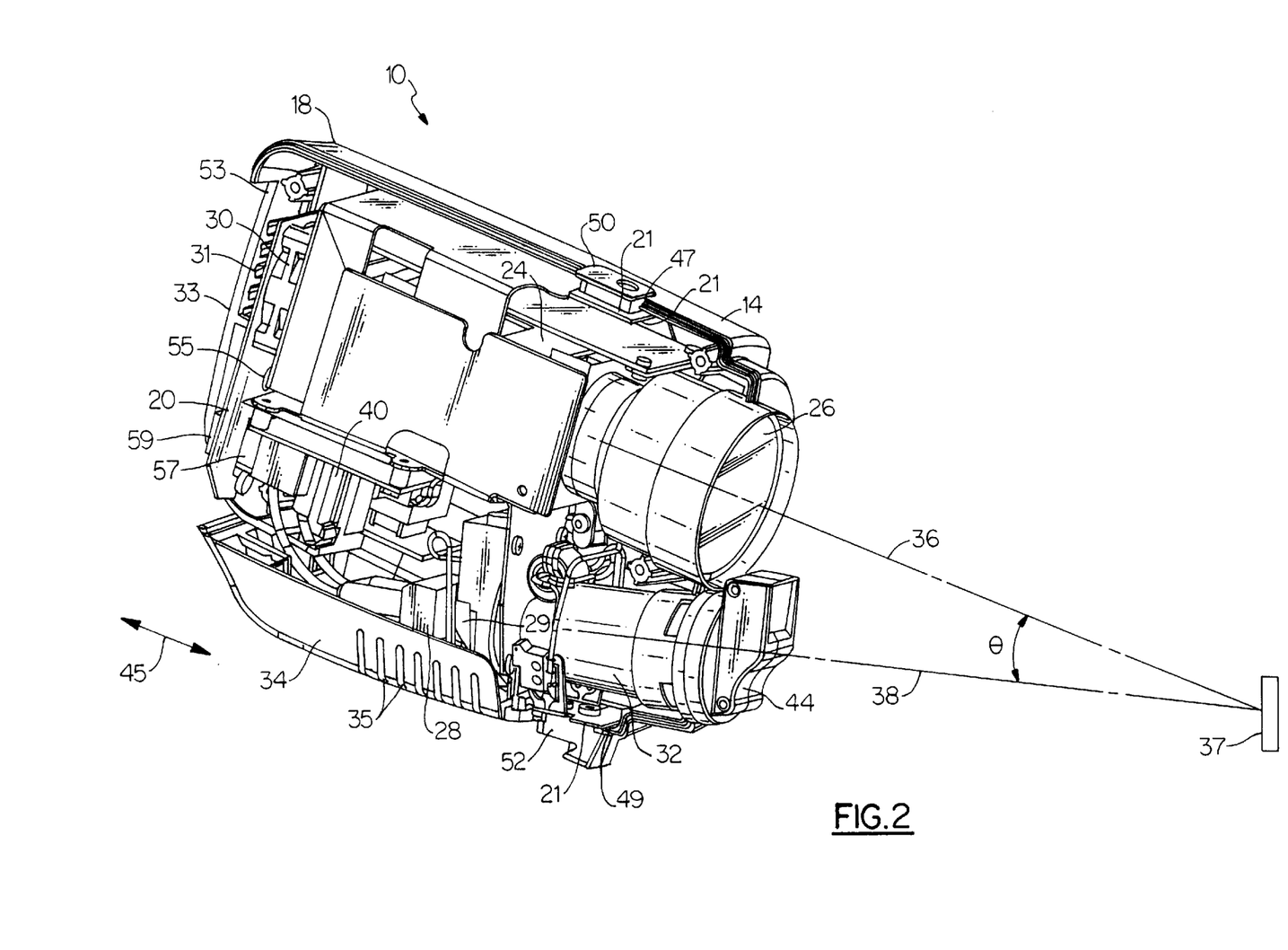
FIG. 2 is a sectional view of the colposcope of FIG. 1.

Referring now to the drawings and specifically to FIGS. 1 and 2, there is shown a compact colposcope 10, having a body or housing 14, preferably consisting of a pair of interconnecting half sections 16, 18. The half sections 16, 18 are preferably manufactured from an injection-molded plastic or other suitable material, sandwiching an interior casing 20 therebetween when assembled, which is used for supporting a number of components. The half sections 16, 18 are conventionally attached to one another using a set of threaded fasteners 22, though other known attaching means can be utilized.

The interior casing 20 is a frame like structure, which as noted above, is used to support a number of components including a compact video camera 24 used for viewing a target 37 through a set of associated optics, including a front lens 26 along a defined optical axis 36. The video camera 24 includes a CCD imager and circuitry for transmitting and storing a viewed image, the focal length of the front lens 26 being approximately 12 inches (≈300 mm). Such cameras are conventionally available, an example of such a camera being the SONY-EVI-330. A cooling fan 30 disposed behind the video camera 24 dissipates heat through a set of slit-like vent openings 31 provided in the rear 33 of the housing 14.

In addition, an off-axis illumination system includes a light source, disposed adjacently beneath the video camera 24 for providing incident white light onto the target 37 located a predetermined distance from the front of the housing 14. For purposes of this embodiment, the light source is a high-intensity, low power (approximately 21 watts) subminiature arc lamp 28, which is described in greater detail in commonly assigned U.S. Pat. No. 5,083,059 (Graham, et al), and which is hereby incorporated by reference. Other light sources, such as an optical fiber bundle (not shown) can alternately be utilized.

According to this embodiment, the incident light from the arc lamp 28 and attached reflector 29 is projected along a defined illumination axis 38 passing through a tubular collimator tunnel 32 at an included angle θ relative to the optical axis 36. Preferably, the respective axes 36, 38 intersect at a point which is approximately the focal point of the front lens 26.

An illumination beam director 44, attached to the housing 14 at the end of the tubular collimator tunnel 32, is used to shift the illumination axis 38 and thereby reduce the angle θ in order to minimize the effects of shadowing during an examination procedure using the colposcope 10 and a speculum (not shown). The details and operation of the illumination beam director 44 are described in copending and commonly assigned U.S. Ser. No. 08/748,374, [Attorney Docket 282231/945429] (Krauter, et al) filed concurrently herewith, the entire contents of which are hereby incorporated by reference. The illumination system also includes a miniature lamp ballast 40, such as described in commonly assigned U.S. Pat. No. 5,291,100 (Wood) which controls the duty cycle and includes a power output sensing and emergency shutdown control circuit. Circuitry in the ballast 40 also provides constant output power to compensate for aging of the lamp 28.

The arc lamp 28 can be accessed, for replacement or other purposes, from the bottom of the housing 14 through a removable lamp door 34 which is snap-fitted to cover an opening provided by the half sections 16, 18 of the housing 14. The lamp door 34 includes a series of slit-like vent openings 35, similar to those provided in the rear of the housing 14, to allow heat to dissipate. The lamp door 34 according to this embodiment is slidingly engageable with the bottom surface 43 of the housing 14 in the direction 45 for assembly and removal therefrom.

A series of external switches 42, 46, and 48 provided on each side of the assembled housing 14 are electrically connected to operate a motorized zoom mechanism (not shown), for focussing the camera optics, and for activating an electronic green filter (not shown). Examples of focussing and zooming systems are extremely well known with many examples present in the field. The electronic green filter is provided to remove red light from the video image, preferably for vascular discrimination, and is described in greater detail in commonly assigned and copending U.S. Ser. No. 08/748,375 (Krauter, et al), filed Aug. 20, 1996. Preferably, the switches 42, 46, and 48 are provided on each side of the housing 14 to allow right handed or left handed operation of the instrument.

Figure 5:
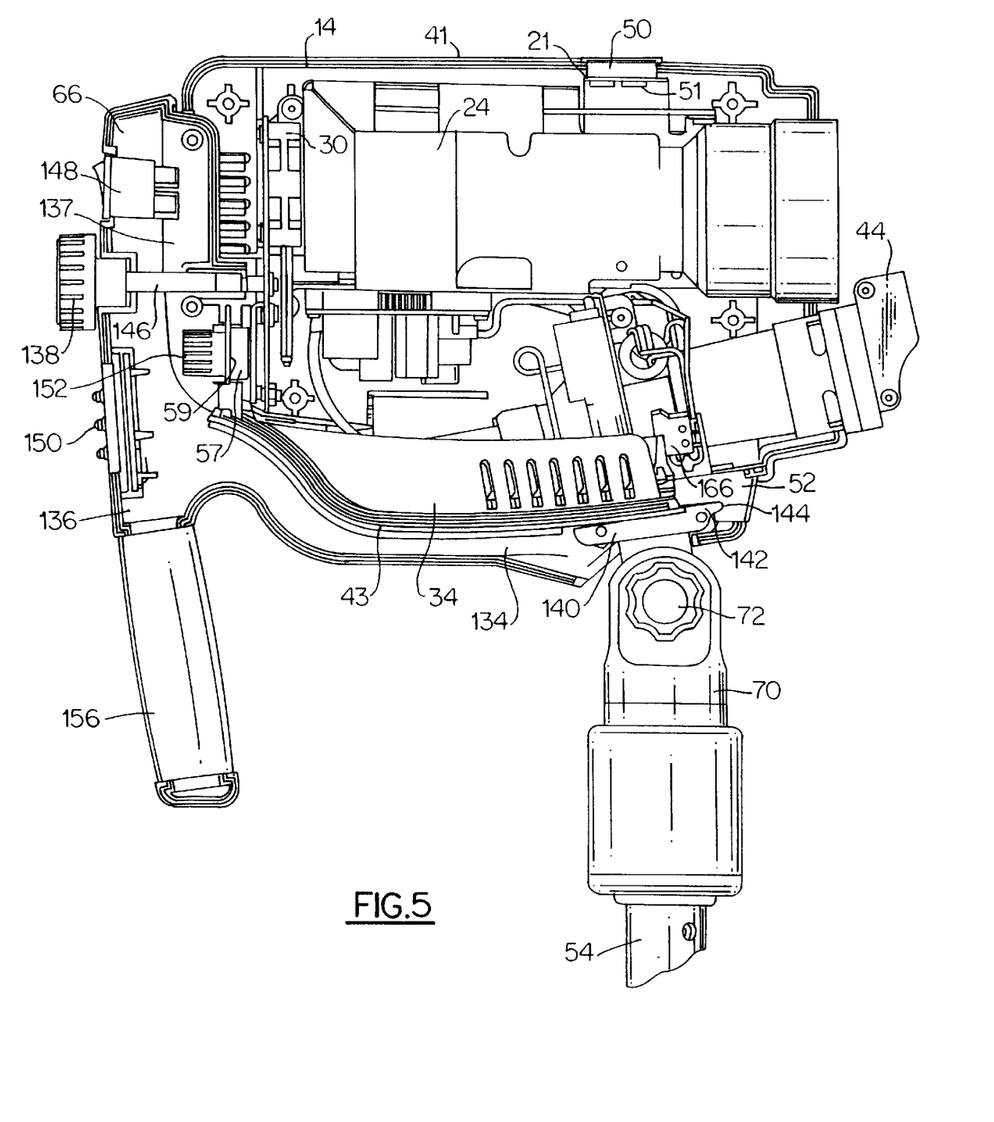
FIG. 5 is a partial side sectional view of the colposcope of FIG. 2, as assembled to the handle portion of the first supporting assembly of FIG. 3.
Figure 7:
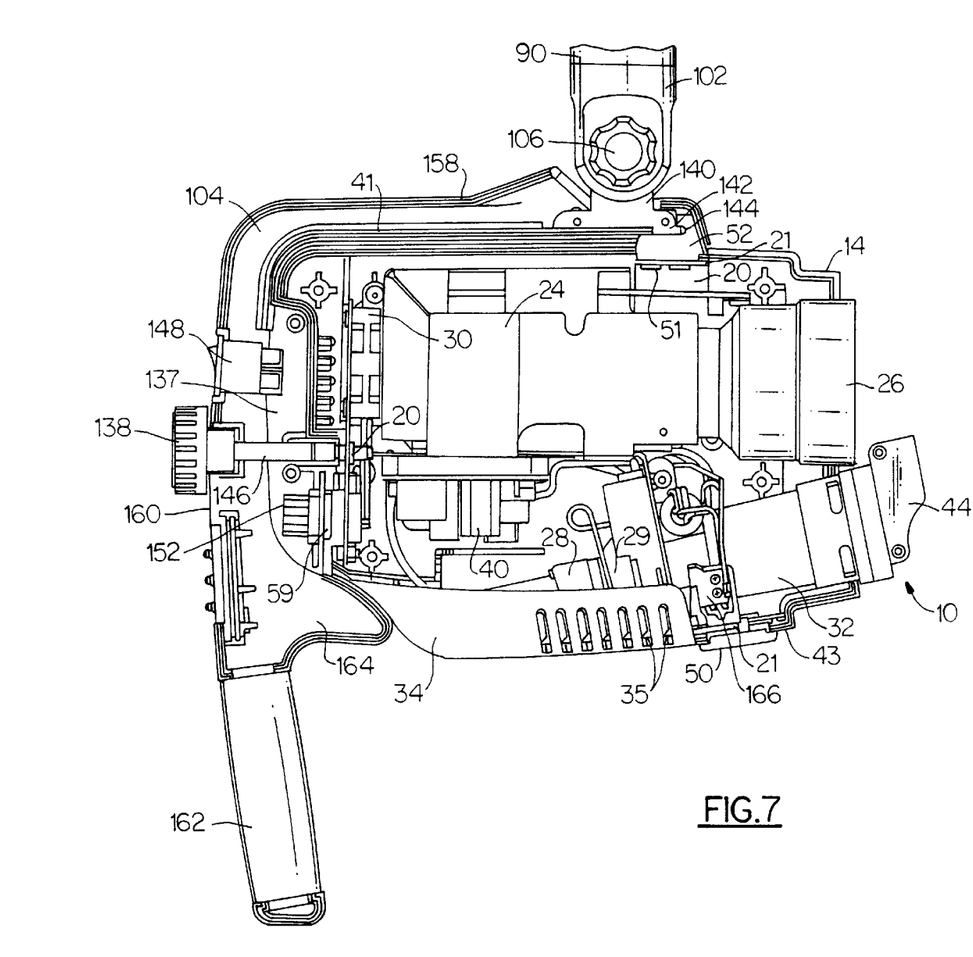
FIG. 7 is a partial side sectional view of the colposcope of FIG. 2, as assembled to the handle portion of the second supporting assembly of FIG. 4.

In addition, the top and bottom surfaces 41, 43 of the housing 14 each include respective openings 47, 49 for interchangeably accommodating a cap 50 and an adaptive toeplate 52, each mountable thereto using threaded fasteners 51, FIGS. 5, 7, to a supporting plate 21 of the internal casing 20. The functions of the cap 50 and toeplate 52 are each described in greater detail below.

Each of the supported components described above include electrical leads (not shown) which are channeled into a single electrical port 57 having an external electrical connecting receptacle 59 supported by a rear portion of the internal casing 20. The receptacle 59 includes a series of terminal pins (not shown), each relating to a specific electrical lead as is known which extend from the rear 33 of the housing 14 and accessible through a slot 53 provided between the housing sections 16, 18. The video output of the CCD imager of the video camera 24 is also connected to the port 57 for transmission as is described below. The rear 33 of the housing 14 also includes a mounting socket 55 for allowing locking engagement with the interfacing handle portion 66, 104, FIGS. 3, 4, of a pair of supporting fixtures 54, 90, FIGS. 3, 4, in conjunction with the adaptive toeplate 52.

When fully assembled, the colposcope 10 defines a compact video/illumination unit weighing about 3.5 lbs (approx. 1.6 kgs) which with the supporting fixtures 54, 90 define a complete diagnostic system. The supporting assemblies 54, 90, will now be described with reference to FIGS. 3–7.

Figure 3:
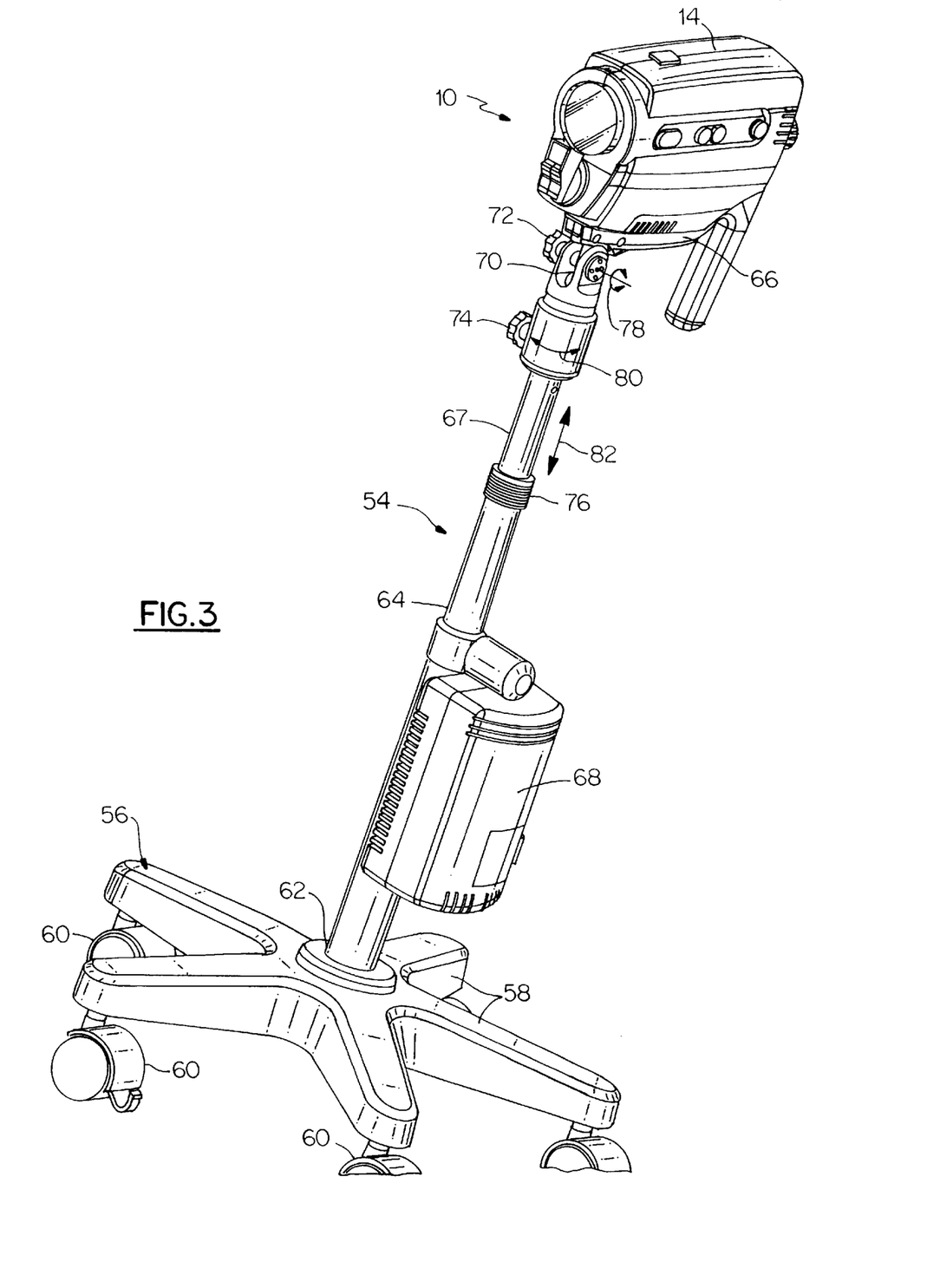
FIG. 3 is a perspective view of the colposcope of FIG. 1, as mounted to a first supporting assembly.

Referring first to FIG. 3, a bottom supporting fixture 54 is shown which includes a base portion 56 including a plurality of legs 58 with depending casters 60 at the ends to allow the fixture to be slidingly movable along a floor or other surface. The base portion 56 includes a center opening 62 for retaining therein a vertical pole 64 having an interior which allows cabling from an attached power supply 68 to be run to an interfacing handle portion 66 pivotally attached to a yoked top end 70 of the pole. The bottom supporting fixture 54 includes a pair of adjusting knobs 72, 74, as well as a friction collar 76, which allow an attached colposcope 10 to be oriented in a versatile manner.

As noted, the bottom supporting fixture 54 allows the mounted colposcope 10 to assume a number of positions. A top adjustment knob 72 includes a screw threaded portion (not shown) permitting the colposcope 10 to tip forward and rearward in the direction 78 when the knob is released by rotation thereof, as is known. Similarly, a second adjustment knob 74, when released, allows the yoked end 70 of the fixture 54 to rotate about the vertical axis of the pole 64 in the direction 80. Finally, the friction collar 76 allows a telescoping portion 67 of the vertical pole 64 to extend or retract in the direction 82 when the collar is loosened by screw engagement with the remainder of the pole 64. Each of the adjustment knobs 72, 74 and the collar 76 can be locked into a selected position by retightening their respective screw threaded portions into place.

Figure 4:
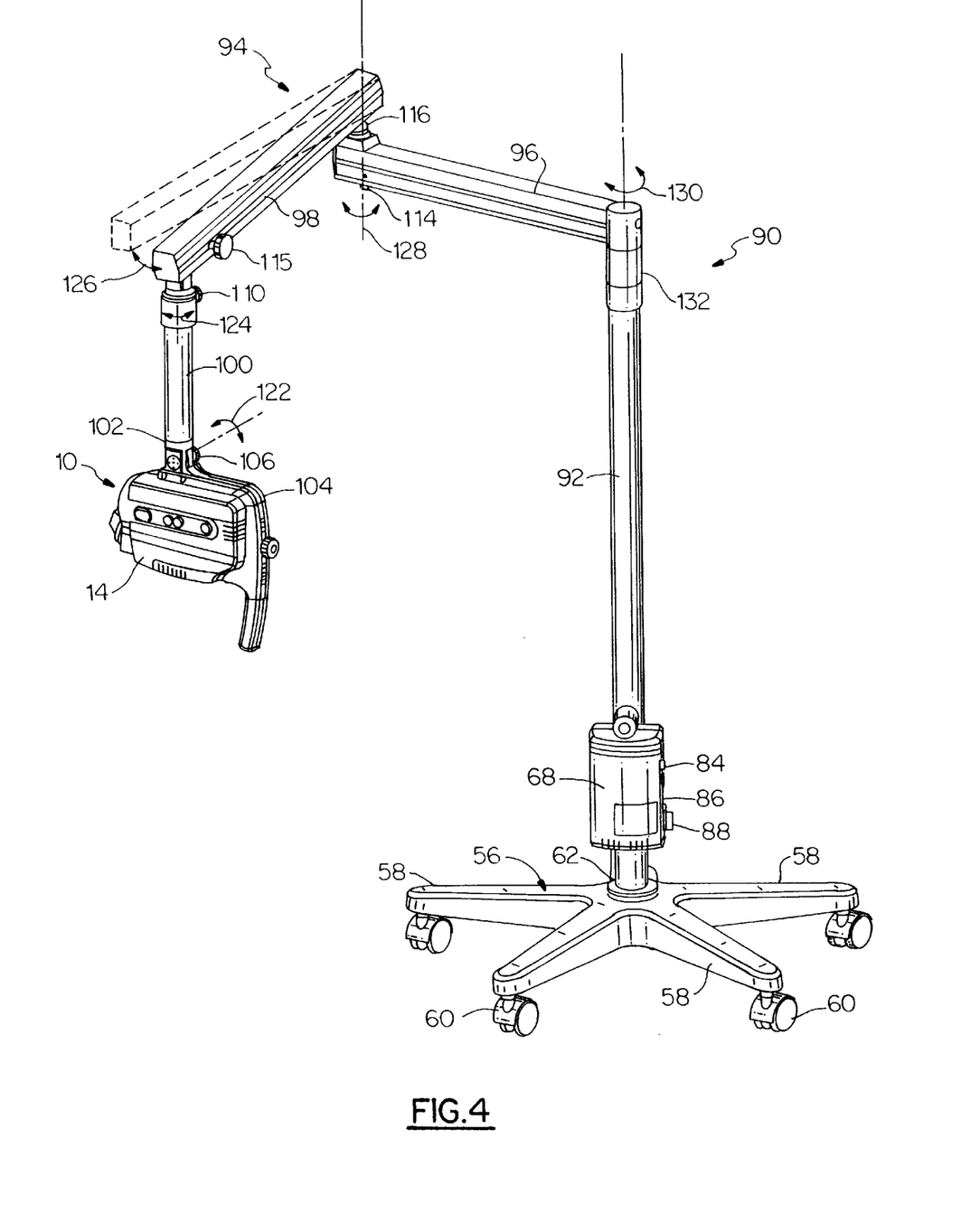
FIG. 4 is a side elevational view of the colposcope of FIGS. 1–2, as mounted to a second supporting assembly.

The power supply 68 is integrally attached to a lower portion of the vertical pole 64 adjacent the base portion 56 and includes a series of external ports 84, 86, and 88, FIG. 4, for interconnecting with an AC power input (not shown) and several peripheral devices, such as a video printer (not shown) and a video monitor (not shown). As is described below, the interior of the power supply 68 contains circuitry for converting the AC power input to low voltage DC. The power supply 68 also complements the peripheral devices with the mounted colposcope 10 using cabling (not shown) that is routed from the interior of the power supply 68 through the vertical pole 64 and into the interfacing handle portion 66, as described in greater detail below.

The top supporting assembly 90 is herein described with reference to FIG. 4. Similar parts which have previously described above are labeled with the same reference numerals for the sake of clarity. That is, the assembly 90 also includes a base portion 56 including a plurality of legs 58 with depending casters 60 at the ends to allow translatable movement along a floor or other surface as well as a center opening 62 provided for retaining a vertical pole 92 therein. The vertical pole 92 according to this embodiment, however, includes a swing arm assembly 94 extending from the top of the pole comprising a pair of articulating horizontal swing arms 96, 98 pivotally interconnected through an attached pivot or axle 116. A vertical support extension 100 depending from the end of the articulating arm 98 includes an interfacing handle portion 104 which is pivotally supported to a yoked end 102 thereof.

A power supply 68, similar to that previously described is disposed at the bottom of the vertical pole 92 adjacent the base portion 56 containing cabling (not shown) which extends through the interior (not shown) of the vertical pole 92. The cabling extends through each of the articulating arms 96, 98, the vertical support extension 100, and the interior of the interfacing handle portion 104 through the yoked end 102 to provide sufficient power for the electrical components housed in the colposcope 10, as well as to allow routing of a video signal from the video camera 24. In addition, the power supply 68 includes externally accessible ports 84, 86, and 88 for connecting to an AC power input (not shown) and a series of compatible peripheral devices, such as a video monitor (not shown) and a video printer (not shown) utilizing the video signal from the video camera 24 of a mounted colposcope 10.

Still referring to FIG. 4, the top supporting fixture 90 also provides for a myriad of possible orientations for an attached colposcope 10. When released, an adjustment knob 106, adjacent the interfacing handle portion 104, allows the attached colposcope 10 to tip in the direction 122 about the yoked end 102. Another similar adjustment knob 110 at the top of the support extension 100 allows the entirety of the support extension, including the supported colposcope 10, to rotate per arrow 124. Each of the adjustment knobs 106, 110 is threaded into engagement to allow locking in a selected position. A third adjustment knob 115 controls a vertical pivoting movement of the second articulating arm 98 about the supported end in the direction 126, shown in phantom.

The second articulating arm 98 is pivotally mounted to the first arm 96 through the axle 116 having an attached stop 114. When the stop 114 is released, the arm 98 can rotate freely about an axis of the axle 116 in the direction 128. When the stop 114 in its normal (unreleased) position, the second articulating arm 98 is precluded from movement through an arc (not shown) in the horizontal plane. This arc is centered about the axle 116 and contains about 45 degrees on either side of the radial extension of the first articulation arm 96.

Finally, the first articulating arm 96 is rotatably mounted to the end of the pole 92 through a collar 132 which allows the entire swing arm assembly 94 to be rotated about the vertical axis of the pole 92, in the direction 130.

Referring to FIG. 5, the interfacing handle portion 66 of the bottom supporting fixture 54 is a substantially L-shaped plastic member, which includes respective bottom and rear retaining sections 134, 136 sized to engage the rear 31 and bottom sides 43, respectively, of the colposcope housing 14. The rear retaining portion 136 includes an extending portion 137 sized to fit within the slot 53, FIG. 2, formed by the half housing sections 16, 18. The extending portion 137 includes an exterior locking knob 138 having a through screw threaded extension 146, and a female electrical connector 152, through which cabling (not shown) from the interior of the power supply 68 is attached.

The exterior of the rear retaining portion 136 includes a power ON/OFF switch 148 interconnected through the female electrical connector 152 and the power supply 68, FIG. 3, as well as an adjacent series of externally accessible remote control buttons 150 for controlling the operation of the peripheral devices (not shown). According to this embodiment, the remote control buttons 150 are used to control a video printer (not shown) interconnected through the external ports 84, 86, FIG. 4, provided on the power supply 68, FIG. 4. Functionally, the buttons 150 control freezing a real-time video image obtained from the video camera 24 on the monitor by use of the video printer, copying the video image on the monitor by use of the video printer, and toggling between the freeze and real-time video modes.

Figure 6:
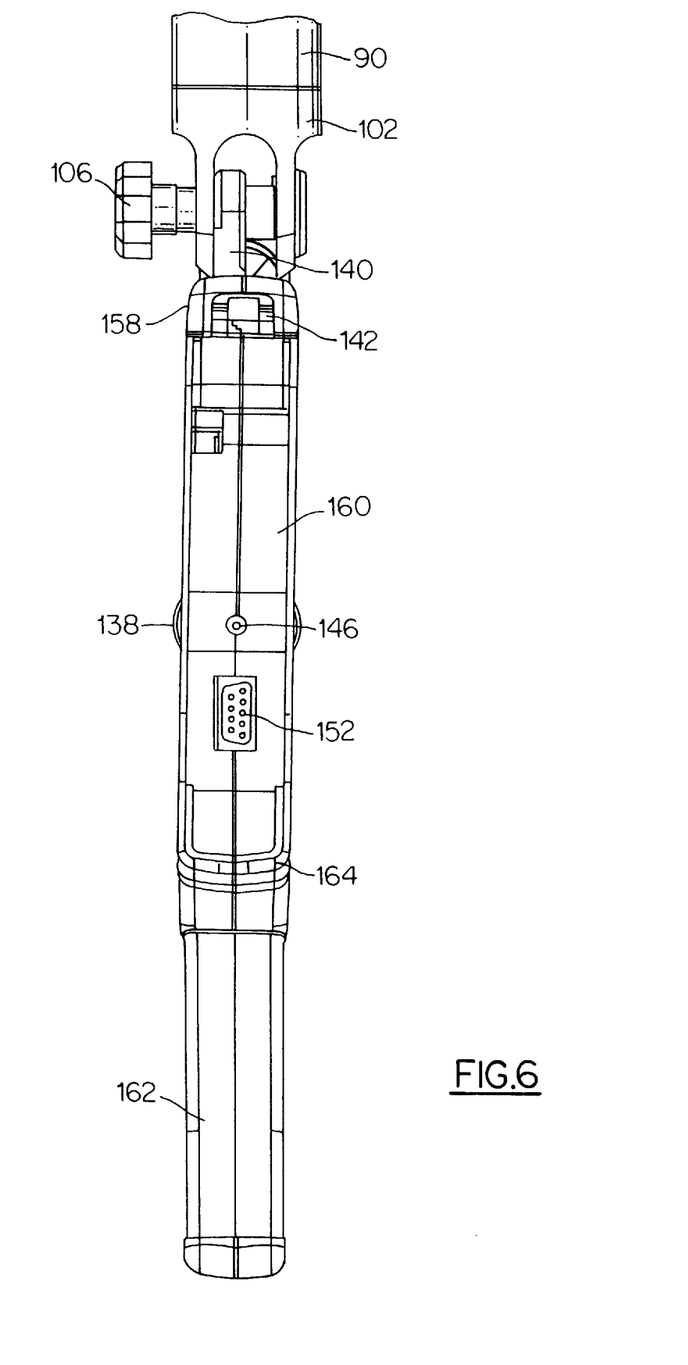
FIG. 6 is a partial front view of the handle portion of the first supporting assembly of FIGS. 3 and 5.

Referring to FIGS. 6 and 7, the interfacing handle portion 104 of the top supporting fixture 90 also includes a pair of retaining portions configured in substantially an L-shape comprising a rear retaining portion 160 and a top retaining portion 158 which are sized to engage the rear and top sides 33, 41, FIG. 2, of a colposcope 10. The rear retaining portion 160 is similar to that previously described including an extending portion 137 sized to engage within the slot 53, FIG. 2, formed by the housing half sections 16, 18 and having an exterior locking knob 138 which includes a screw threaded portion 146 extending toward and through the extended portion 137. The extending portion 137 also includes a female electrical connector 152 to which the cabling (not shown) from the power supply 68, FIG. 4, has been connected, as is known.

The top retaining portion 158 is sized to fit a substantial length of the housing 14 and includes a supporting plate 140 having an engagement section including an extending end 142, similar to that described in the bottom supporting fixture 54, FIG. 5. The supporting plate 140 extends from the yoked end 102 of the vertical support extension 100, FIG. 4.

Referring now to FIGS. 2, 3, and 5, the attachment of the colposcope 10 to the bottom supporting fixture 54 is herein described. It is assumed that the toeplate 52 is already engaged in the bottom side 43 of the housing 14. The interfacing handle portion 66 of the bottom supporting fixture 54 is attached to the rear side 33 of the colposcope housing 14 by engaging the extending portion 137 of the rear retaining portion 136 into the slot 53, FIG. 2, while subsequently threading the screw threaded extension 146 of the knob 138 into the mounting socket 55. The female electrical connector 152 is automatically aligned and engaged with the externally disposed receptacle 59. At the same time, the bottom side 43 of the housing 14 is supported by attachment of the extending end 142 of the support plate 140 located on the bottom retaining portion 134 within the recessed portion 144 of the toeplate 52. A handle 156 on the lower end of the rear retaining portion 136 allows movement in the manner previously described.

The attachment of the colposcope 10 to the top supporting fixture 90 is herein described with reference to FIGS. 2, 4, 6, and 7. This description assumes the colposcope 10 has been removed from the bottom supporting fixture 54. The cap 50 is first removed from the top opening 47 of the colposcope housing 14 by loosening the threaded engagement between the fasteners 51, FIG. 5, and the supporting plate 21 of the internal casing 20, and the toe plate 52 is similarly removed from the bottom opening 49. The positions of the toeplate 52 and the cap 50 are then reversed with the toe plate inserted and fastened into engagement in the top opening 47.

The recessed portion 144 of the toeplate 52 is aligned with the extending portion 142 of the supporting plate 140, which is a part of the top retaining portion 158 of the interfacing handle portion 104. At the same time, the extending portion 137 of the rear retaining portion 160 is aligned with the slot 53 in the rear 33 of the housing 14 and the screw extending portion 146 of the knob 138 is aligned with the mounting socket 55. The knob 138 is rotated to engage the screw threaded portion 146 into locking engagement with the housing 14, retaining the colposcope 10 in place. The female electrical connector 152 is automatically aligned and engaged with the externally disposed receptacle 59.

In use, the lamp door 34 is prevented from opening when the colposcope housing 14 is attached to either supporting fixture 54, 90. In the case of the top supporting fixture 90, and referring to FIG. 7, the interfacing handle portion 104 includes a lamp door retaining portion 164 adjacent the handle 162 for pressing against the rear of the lamp door 34 when the colposcope 10 is mounted to the top supporting fixture 90. In the case of the bottom supporting fixture 54, the bottom retaining portion 134 covers the entirety of the lamp door 34 and prevents opening when the colposcope is attached as previously described.

In addition, and referring to FIGS. 5 and 7, the colposcope 10 contains a safety feature comprising a pair of microswitches 166 inside the housing 14 and placed in active engagement with the lamp circuit to close the circuit when the lamp door 34 is installed on the colposcope housing 14. The switches 166 are biased to open when the lamp door 34 is removed from the housing 14, such as to access the lamp for replacement, thereby preventing operation of the high intensity arc lamp 28 should the lamp door remain uninstalled when the colposcope 10 is attached to either supporting fixture 54, 90.

PARTS LIST FOR FIGS. 1–7

PARTS LIST FOR FIGS. 1–7

- 10 compact colposcope
- 14 housing
- 16 half section
- 18 half section
- 20 interior casing
- 21 supporting plate
- 22 threaded fasteners
- 24 video camera
- 26 front lens
- 28 arc lamp
- 30 cooling fan
- 31 openings
- 32 collimating tunnel
- 33 rear-housing
- 34 lamp door
- 35 openings
- 36 optical axis
- 38 illumination axis
- 40 ballast
- 41 top surface
- 42 switches
- 43 bottom surface
- 44 illumination beam director
- 45 direction
- 46 switches
- 47 opening
- 48 switches
- 49 opening
- 50 cap
- 51 threaded fasteners
- 52 toeplate
- 53 slot
- 54 bottom supporting fixture
- 55 mounting bracket
- 56 base portion
- 57 port
- 58 legs
- 59 receptacle
- 60 casters
- 62 center opening
- 64 pole
- 66 interfacing handle portion
- 67 telescoping section
- 68 power supply
- 70 yoked end
- 72 adjustment knob
- 74 adjustment knob
- 76 collar
- 78 direction
- 80 direction
- 82 direction
- 84 port
- 86 port
- 88 port
- 90 top supporting fixture
- 92 vertical pole
- 94 swing arm assembly
- 96 articulating arm
- 98 articulating arm
- 100 support extension
- 102 yoked end
- 104 interfacing handle portion
- 106 adjustment knob
- 110 adjustment knob
- 114 stop
- 115 adjustment knob
- 116 pivot/axle
- 122 direction
- 124 arrow
- 126 direction -continued

PARTS LIST FOR FIGS. 1–7

128 direction
130 direction
132 collar
134 bottom retaining portion
136 rear retaining portion
137 extending portion
138 locking knob
140 support plate
142 extending portion
144 recessed portion
146 screw threaded portion
148 power switch
150 remote control buttons
152 female electrical connector
156 handle
158 top retaining portion
160 rear retaining portion
162 handle
164 lamp door retaining portion
166 microswitches While the invention has been explained with reference to the structure disclosed herein, it is not confined to the details set forth, and this application is intended to cover any modifications and changes as may come within the scope of following claims:

We claim:

1. A diagnostic instrument system comprising:

a diagnostic instrument, said instrument having a housing including an interior, an illumination system arranged within said interior for illuminating a target, and a video camera system adjacently arranged within said interior relative to said illumination system for viewing the illuminated target;

at least two supporting fixtures, said supporting fixtures each having a handle portion engageable with different surfaces of said housing for attachment thereto; and means for releasably attaching said housing to each one of said supporting fixtures, wherein each of said handle portions include releasable connecting means for mating with the housing to mechanically support said diagnostic instrument to provide electrical and video connection therewith.

2. A diagnostic instrument system as recited in claim 1, wherein said releasable attachment means includes an adapter member engageable with said housing and each of said housing portions, said adapter member being separately attachable and removable from different surfaces of said housing.

3. A diagnostic instrument system according to claim 2, wherein said instrument is a colposcope.

4. A colposcope assembly comprising:

a colposcope including a housing having an interior, an illumination system for illuminating a target and an optical system for viewing said target, said illumination and optical systems being disposed adjacently within said housing;

a first supporting fixture for supporting said colposcope housing;

a second supporting fixture for supporting said colposcope housing; and adapter means for selectively attaching said colposcope housing to either of said supporting fixtures, wherein said first and second supporting fixtures each include a handle portion, said optical system including a video camera and in which said handle portions each contain connecting means for electrically and optically connecting to said illumination system and said optical system and to allow a video signal from said video camera to be transmitted external to said housing.

5. A colposcope assembly as recited in claim 4, wherein said handle portion of said first supporting fixture includes means for attaching to a rear surface and a bottom surface of said colposcope housing, and said handle portion of said second supporting fixture includes means for attaching to said rear surface and a top surface of said colposcope housing.

6. A colposcope assembly as recited in claim 5, wherein said colposcope housing includes an opening in each of said bottom and top surfaces, said opening being sized for said adapter means.

7. A colposcope assembly as recited in claim 6, wherein said adapter means includes an intermediate member which is mountable in a said opening of said housing and includes means for attaching to one of said handle portions to interconnect said colposcope housing and one of said supporting fixtures.

8. A colposcopic system comprising:

a compact colposcope body having an interior for containing therein an illumination system and an adjacently arranged optical system disposed therein; said optical system including a video camera; and a pair of supporting stand assemblies wherein said body includes means for allowing the colposcope to be selectively attached to either supporting stand assembly, each supporting stand assembly including a handle portion having releasable connecting means for mating with the colposcope body to mechanically support the colposcope and to provide electrical and video connection therewith.

9. A colposcope system as recited in claim 8, wherein one said supporting stand assembly is a swing arm supporting fixture having a handle portion for supporting the colposcope body at top and rear surfaces.

10. A colposcope system as recited in claim 9, wherein the other of said supporting stand assemblies includes means for supporting a bottom and a rear surface of said colposcope body.

* * * * *